United States Patent
Thakur et al.

(10) Patent No.: US 10,405,826 B2
(45) Date of Patent: Sep. 10, 2019

(54) METHODS AND SYSTEM FOR TRACKING HEART SOUNDS

(71) Applicant: Cardiac Pacemakers, Inc., St. Paul, MN (US)

(72) Inventors: Pramodsingh Hirasingh Thakur, Woodbury, MN (US); Qi An, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 542 days.

(21) Appl. No.: 14/983,867

(22) Filed: Dec. 30, 2015

(65) Prior Publication Data

US 2016/0192888 A1 Jul. 7, 2016

Related U.S. Application Data

(60) Provisional application No. 62/099,279, filed on Jan. 2, 2015.

(51) Int. Cl.
*A61B 7/04* (2006.01)

(52) U.S. Cl.
CPC ..................... *A61B 7/04* (2013.01)

(58) Field of Classification Search
CPC .......... A61B 7/04; A61B 5/0225; A61B 5/025
USPC ................................ 600/508, 514
See application file for complete search history.

(56) References Cited

U.S. PATENT DOCUMENTS

| | | | |
|---|---|---|---|
| 5,792,195 A | 8/1998 | Carlson et al. | |
| 7,853,327 B2 | 12/2010 | Patangay et al. | |
| 7,972,275 B2 | 7/2011 | Siejko et al. | |
| 8,211,033 B2 | 7/2012 | Siejko et al. | |
| 8,211,034 B2 | 7/2012 | Patangay et al. | |
| 8,257,271 B2 | 9/2012 | Siejko et al. | |
| 8,317,717 B2 | 11/2012 | Siejko et al. | |
| 8,332,034 B2 | 12/2012 | Patangay et al. | |
| 8,500,650 B2 | 8/2013 | Siejko et al. | |
| 2008/0262368 A1* | 10/2008 | Patangay | A61B 7/04 600/528 |
| 2011/0077543 A1 | 3/2011 | Patangay et al. | |
| 2013/0096451 A1 | 4/2013 | Patangay et al. | |

FOREIGN PATENT DOCUMENTS

WO WO-2008130532 A1 10/2008

* cited by examiner

*Primary Examiner* — Michael J Carey
(74) *Attorney, Agent, or Firm* — Schwegman Lundberg & Woessner, P.A.

(57) ABSTRACT

Systems and methods for tracking heart sounds are disclosed. The system can include a heart sound (HS) receiver circuit configured to receive HS information, and a HS analyzer circuit coupled to the HS receiver circuit. The HS analyzer circuit can determine a HS timing parameter of a specified HS component. The HS component includes at least a portion of one of S1 S2, S3, or S4 heart sound. The HS analyzer circuit can include first and second feature detector circuits each configured to respectively detect first and second one or more candidate features. The HS analyzer circuit can also include a feature selection circuit that can produce an inter-categorical metric, and determine first and second selected features using at least the inter-categorical metric. A HS recognition circuit can determine the timing parameter of the HS component using the first and second selected features.

20 Claims, 5 Drawing Sheets

METHODS AND SYSTEM FOR TRACKING HEART SOUNDS

CLAIM OF PRIORITY

This application claims the benefit of priority under 35 U.S.C. § 119(e) of U.S. Provisional Patent Application Ser. No. 62/099,279, filed on Jan. 2, 2015, which is herein incorporated by reference in its entirety.

TECHNICAL FIELD

This document relates generally to cardiac health, and more particularly, but not by way of limitation, to heart sounds tracking.

BACKGROUND

Heart sounds are generally associated with the mechanical vibrations from the activity of a subject's heart and the flow of blood through the heart. Because of this association, heart sounds typically recur with each cardiac cycle of a heart, and are typically separated and classified into one of four components according to the activity associated with the vibration: S1, S2, S3, and S4. S1 component (commonly referred to in the art as "the first heart sound") is typically associated with the vibrational sound made by the heart during tensing of the mitral valve. S2 component (commonly referred to in the art as "the second heart sound") is typically associated with the beginning of diastole. S3 component (commonly referred to in the art as "the third heart sound") and S4 component (commonly referred to in the art as "the fourth heart sound") are typically associated with the filling pressures of the left ventricle during diastole. Generally, heart sounds can be used as indications of proper or improper functioning of a subject's heart, and can thus be used for diagnosing various heart diseases.

Overview

A heart sound, including one or more of S1, S2, S3, or S4 components, can typically be characterized by heart sound signal intensity and corresponding timing. Timing information of a particular heart sound component can be useful in determining physiologic parameters indicative of cardiac function or progression of a heart disease. One example of such timing information is a systolic timing interval (STI). The STI represents duration of total electro-mechanical systole, spanning from the electrical excitation of the heart to the closure of the aortic valve. The STI contains two major components, namely the PEP and the LVET. The PEP, representing the total duration of the electrical and mechanical events prior to ejection, can include the electrical-mechanical delay which occurs between the onset of the ventricular depolarization and the beginning of ventricular contraction, and the isovolemic contraction time during which the left ventricle can contract prior to the opening of the aortic valve. The LVET represents the time interval from the opening to the closing of the aortic valve (mechanical systole). The STI has been shown to be correlated to myocardial contractility. Therefore, a trend of STI over a period of time can be clinical indices in evaluating cardiac performance in patient with heart disease such as congestive heart failure (CHF).

Timing of heart sound components, such as S1 and S2 components, can be used in measuring STI or other cardiac timing intervals. In an example, STI can be measured as an interval from the onset of the QRS complex of an electrocardiogram (ECG) signal, or other cardiac activation event such as an atrial or ventricular pacing event which can be detected from an intracardiac electrogram (EGM), to an S2 heart sound component within the same cardiac cycle, that is, STI≈Q-S2 interval. In an example, the PEP can be measured as the time duration from the onset of the QRS on an ECG, or other cardiac activation event such as an atrial or ventricular pacing event which can be detected from an EGM, to the S1 heart sound, that is, PEP≈Q-S1 interval. The LVET can be measured as the time duration from S1 to S2 heart sounds, that is, LVET≈S1-S2 interval.

A heart sound component, such as S1, S2, S3 or S4 heart sound, can be detected using a heart sound window established according to certain triggering events, such as certain components of an ECG signal. Detection and identification of a particular heart sound component of interest can involve detecting the maximum heart sound intensity, such as signal amplitude or signal power of a signal peak within a heart sound window corresponding to the heart sound component of interest. The timing of the peak with the maximum intensity can then be determined as the timing of the heart sound component of interest.

However, the present inventors have recognized that the method of detecting the peak in the heart sound window having the maximum amplitude may not be a desirable identifier of the heart sound component of interest. A heart sound signal, or a portion of the heart sound signal within the heart sound window, may contain multiple peaks. The relative strength of signal intensities of these peaks (e.g., amplitude) may vary substantially from one cardiac cycle to another. As such, timing of the peak with the greatest amplitude, and thus the timing of the HS component of interest, can be less consistent over time. This may reduce the predictive power of parameters computed using the HS component timing, such as STI. The timing inconsistency of the HS component is not only a challenge for the method based on peaks with maximum amplitude, but can also persist in other HS component detecting methods using a HS window in isolation, or exclusively within a portion of the heart sound signal in a cardiac cycle. The present inventors have recognized that there remains a need to improve the consistency of HS component detection, and thereby improving predictive power of a trend of HS component timing in assessing heart diseases such as worsening of HF.

This document discusses, among other things, a system and method for tracking heart sounds, including an input circuit for receiving heart sound (HS) information, and a heart sound analyzer circuit for determining a HS timing parameter of a specified HS component, such as one of S1 S2, S3, or S4 heart sound. The HS analyzer circuit can detect a first feature set including one or more candidate features and a second feature set including one or more candidate features, produce an inter-categorical metric, and select first and second selected features from the respective feature set using at least the inter-categorical metric. A HS recognition circuit determines the timing parameter of the HS component using the first and second selected features.

In Example 1, a system can comprise a heart sound (HS) receiver circuit that can be configured to receive HS information including at least one HS waveform, and can comprise a HS analyzer circuit that can be coupled to the HS receiver circuit. The HS analyzer circuit can determine a HS timing parameter of a specified HS component within the HS waveform. The specified HS component can include at least a portion of one of S1, S2, S3, or S4 heart sound. The HS analyzer circuit can include a first feature detector circuit, a second feature detector, a feature selection circuit, and a HS recognition circuit. The first and second feature detector circuits can each be configured to respectively detect first one or more candidate features and second one or more candidate features within the HS waveform. Each candidate feature can include a respective feature timing indication and a respective feature intensity indication. The feature selection circuit can produce an inter-categorical metric indicative of temporal relationship between the first and the second sets of candidate features, and can select first and second selected features respectively from the first and second candidate feature set, such as using at least the inter-categorical metric. The HS recognition circuit can determine the HS timing parameter of the specified HS component using a comparison between the first and second selected features.

In Example 2, the first one or more candidate features of Example 1 include one or more peaks within a specified portion of the at least one HS waveform, and the second one or more candidate features of Example 1 include one or more troughs within a specified portion of the at least one HS waveform.

In Example 3, the system of any one of Examples 1 or 2 further comprises an inter-categorical feature analyzer circuit, coupled to the feature selection circuit, which computes the inter-categorical metric. The feature selection circuit of Example 1 or 2 determines the first or second selected feature at least in response to the inter-categorical metric meeting a specified criterion.

In Example 4, the inter-categorical metric of Example 3 includes a temporal offset between a first timing indication of the first candidate feature and a second timing indication of the second candidate feature, and the feature selection circuit determines the first or second selected feature in response to the temporal offset falling outside a respectively specified range.

In Example 5, the system of Example 4 further comprises a temporal offset tracker circuit that computes a reference temporal offset using one or more historical temporal offsets associated with a plurality of historical HS waveforms. The feature selection circuit determines the first or second selected feature in response to the temporal offset falling within a specified margin of the reference temporal offset.

In Example 6, the temporal offset tracker circuit of Example 5 can compute the reference temporal offset as a central tendency of the one or more of the historical temporal offsets.

In Example 7, the system of any one of Examples 4 through 6 further comprises first and second variability analyzer circuits. The first variability analyzer circuit determines a first variability index indicating a deviation of the first timing indication from a first reference timing indication, and the second variability analyzer circuit determines a second variability index indicating a deviation of the second timing indication from a second reference timing indication. The feature selection circuit determines the first selected feature in response to (1) the temporal offset falling outside the respectively specified range and (2) the first variability index exceeds the second variability index by a first specified margin; or determines the second selected feature in response to (1) the temporal offset falling outside the respectively specified range and (2) the second variability index exceeds the first variability index by a second specified margin.

In Example 8, at least one of the first or second reference timing indications of Example 7 can be computed as a central tendency of one or more historical timing indications associated with a plurality of historical HS waveforms.

In Example 9, the feature selection circuit of any one of Examples 7 or 8 selects from the first one or more candidate features the first selected feature that minimizes the first variability index, or selects from the second one or more candidate features the second selected feature that minimizes the second variability index.

In Example 10, the HS recognition circuit of any one of Examples 1 through 9 determines the HS timing parameter of the specified HS component as feature timing indication of the first selected feature if feature intensity indication of the first selected feature exceeds the feature intensity indication of the second selected feature.

In Example 11, the at least one HS waveform of any one of Examples 1 through 10, includes an ensemble average of a heart sound signal over multiple physiological cycles.

In Example 12, the multiple physiological cycles of Example 10 includes multiple cardiac cycles.

In Example 13, the first and second feature detectors of any one of Examples 1 through 12 respectively detects the first and second one or more candidate features within a time window associated with the specified HS component, the time window determined with reference to a physiologic event.

In Example 14, the system of any one of Examples 1 through 13 further comprises a physiologic sensor coupled to the HS receiver circuit. The physiologic sensor detects acoustic or mechanical vibration of at least a portion of a heart indicative of heart sound.

In Example 15, the physiologic sensor of Example 14 includes one of an accelerometer sensor or an acoustic sensor.

In Example 16, a method includes receiving HS information including at least one HS waveform, and detecting first one or more candidate features and different second one or more candidate features within the at least one HS waveform. The first one or more candidate features and the second one or more candidate features each includes a respective feature timing indication and a respective feature intensity indication. The method also includes computing an inter-categorical metric indicative of temporal relationship between the first one or more candidate features and the second one or more candidate features. Using at least the inter-categorical metric, the method determines a first selected feature from the first one or more candidate features, or a second selected feature from the second one or more candidate features. The method also includes determining a HS timing parameter of the specified HS component using a comparison between the first and second selected features. The specified HS component includes at least a portion of one of S1 S2, S3, or S4 heart sound within the at least one HS waveform.

In Example 17, the HS information of Example 16 includes at least one ensemble average of a heart sound signal over multiple physiological cycles.

In Example 18, the method of detecting first and second one or more candidate features of any one of Examples 16 or 17 includes detecting one or more peaks within a specified portion of the at least one HS waveform, and detecting one or more troughs within a specified portion of the at least one HS waveform.

In Example 19, the method of computing the inter-categorical metric of any one of Examples 16 through 18 includes computing a temporal offset between a first timing indication of the first candidate feature and a second timing indication of the second candidate feature. The method of determining the first or second selected feature of any one of Examples 16 through 18 includes determining the first or second selected feature in response to the temporal offset falling outside a respectively specified range.

In Example 20, the method of any one of Examples 16 through 19 further includes computing a reference temporal offset using one or more historical temporal offsets associated with a plurality of historical HS waveforms, and determining the first or second selected feature in response to the temporal offset falling within a specified margin of the reference temporal offset.

In Example 21, the method of any one of Examples 16 through 20 further includes determining first and second variability indices. The first variability index indicates deviation of the first timing indication from a first reference timing indication. The second variability index indicates a deviation of the second timing indication from a second reference timing indication. The method of determining the first or second selected feature of any one of Examples 16 through 20 includes determining the first selected feature in response to (1) the temporal offset falling outside the respectively specified range and (2) the first variability index exceeds the second variability index by a first specified margin; or determining the second selected feature in response to (1) the temporal offset falling outside the respectively specified range and (2) the second variability index exceeds the first variability index by a second specified margin.

In Example 22, the determining the first and second selected features of Example 21 includes selecting from the first one or more candidate features the first selected feature that minimizes the first variability index, or selecting from the second one or more candidate features the second selected feature that minimizes the second variability index.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting and tracking heart sounds. The systems and methods discussed in this document can be used to improve the consistency of detected timing of a specified HS component, such as the timing of S1, S2, S3, or S4 heart sound. The heart sound discussed in this document can include audible or inaudible mechanical vibrations caused by cardiac activity. The heart sound signals can be sensed with a physiologic sensor such as an accelerometer. Such mechanical vibrations can be conceptualized as providing acoustic energy. According to the present document, a first and a different second set of one or more candidate features can be detected within a heart sound signal, and an inter-categorical metric between the first and second sets of features can be computed. By tracking changes of the first and second sets of candidate features and changes of the inter-categorical metric over time, the disclosed systems and methods can determine timing of the specified HS component from the first and second sets of candidate features.

Figure 1:
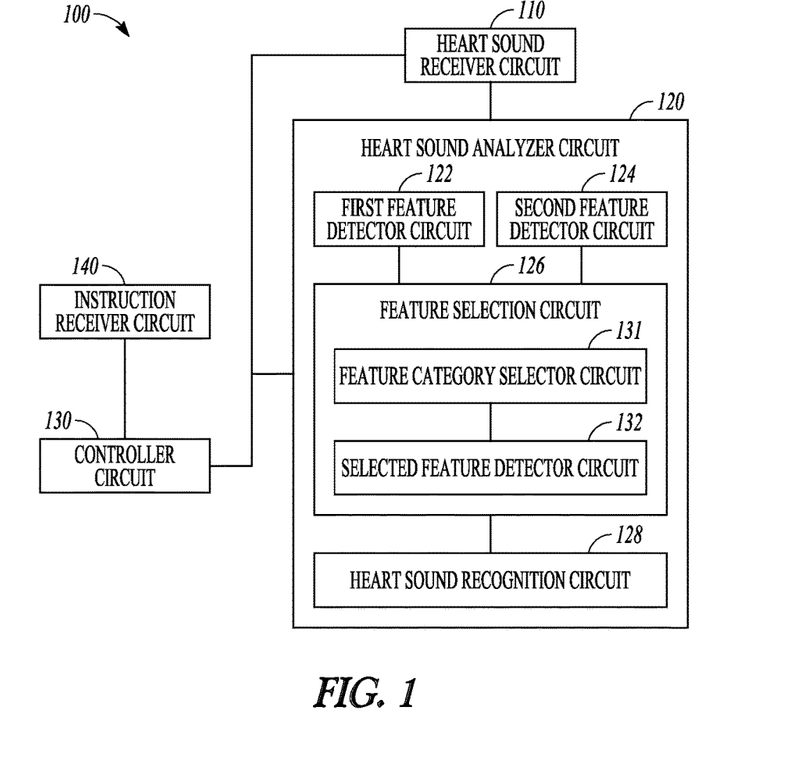
FIG. 1 illustrates an example of a heart sound tracking system.

FIG. 1 illustrates an example of a heart sound tracking system 100, which can include one or more of a heart sound receiver circuit 110, a heart sound analyzer circuit 120, a controller circuit 130, and an instruction receiver circuit 140.

The heart sound (HS) receiver circuit 110 can be configured to receive HS information, such as information indicative of acoustic or mechanical activity of a heart. In an example, the HS information can include a HS waveform, such as a portion or entirety of a HS signal. The HS information can include information of at least one HS component, such as S1, S2, S3, or S4 heart sound. In an example, the HS waveform can include at least one ensemble average of a HS signal over multiple physiological cycles such as multiple cardiac cycles, or over a specified time period such as one minute, ten minutes, one hour, one day, etc.

The HS receiver circuit 110 can be coupled to one or more physiologic sensors that can be configured to sense, detect, or otherwise obtain HS information from a subject. Such physiologic sensors, hereinafter referred to as "HS sensors", can be configured to sense an electrical or optical HS signal that includes information indicative of acoustic or mechanical vibration of a heart. The HS sensor can be an implantable, wearable, or otherwise ambulatory sensor, and placed external to the patient or implanted inside the body. In an example, the HS sensor can be included in at least one part of an implantable system, such as an implantable medical device, or a lead coupled to the implantable medical device. In an example, the HS receiver circuit 110 can be configured to receive the HS information from a device capable of collecting or storing the HS information. Examples of such a device can include an external programmer, an electronic medical record system, a memory unit, or other data storage devices.

Various physiologic sensors can be used to sense the HS signal. In an example, the HS sensor can include an accelerometer that can be configured to sense an acceleration signal indicative of the heart sound of the subject, such as that disclosed in the commonly assigned Carlson et al. U.S. Pat. No. 5,792,195 entitled "ACCELERATION SENSED SAFE UPPER RATE ENVELOPE FOR CALCULATING THE HEMODYNAMIC UPPER RATE LIMIT FOR A RATE ADAPTIVE CARDIAC RHYTHM MANAGE- MENT DEVICE," which is hereby incorporated by reference in its entirety including its disclosure of accelerometer detection of heart sounds. In another example, the HS sensor can include an acoustic sensor that can be configured to sense an acoustic energy indicative of the heart sound of the subject, such as that disclosed in the commonly assigned Siejko et al. U.S. Pat. No. 7,972,275, entitled "METHOD AND APPARATUS FOR MONITORING OF DIASTOLIC HEMODYNAMICS," which is hereby incorporated by reference in its entirety including its disclosure of accelerometer detection of heart sounds. Other sensors, such as microphone, piezo-based sensor, or other vibrational or acoustic sensors can also be used to sense the HS signal.

The heart sound analyzer circuit 120, coupled to the HS receiver circuit 110, can be configured to determine at least a HS timing parameter of a specified HS component within at least one HS waveform, such as by using the HS information from the HS receiver circuit 110. The heart sound analyzer circuit 120 can be implemented as a part of a microprocessor circuit in the heart sound tracking system 100. The microprocessor circuit can be a dedicated processor such as a digital signal processor, application specific integrated circuit (ASIC), microprocessor, or other type of processor for processing information including heart sounds. Alternatively, the microprocessor circuit can be a general purpose processor that can receive and execute a set of instructions of performing the functions, methods, or techniques described herein. The heart sound analyzer circuit 120 can include one or more of a first feature detector circuit 122, a second feature detector 124, a feature selection circuit 126, and a heart sound recognition circuit 128.

The heart sound analyzer circuit 120 can include an optional signal conditioning circuit that can pre-process a HS signal such as received from the HS receiver circuit 110. The pre-processing can include amplification, digitization, filtering, or other signal conditioning operations. In an example, the signal conditioning circuit can include a bandpass filter adapted to filter the received HS signal to a frequency range of approximately between 5 and 90 Hz. In another example, the signal conditioning circuit can include a bandpass filter adapted to filter the received HS signal to a frequency range of approximately between 9 and 90 Hz. In an example, the signal conditioning circuit can include a double or higher-order differentiator configured to calculate a double or higher-order differentiation of the received HS signal.

The first feature detector circuit 122 can be configured to detect a first set of one or more candidate features $\{X_i\}$ such as within a HS waveform, where "i" denotes a feature index in the first candidate feature set. The first candidate feature set $\{X_i\}$ can include statistical or morphological features, such as characteristic points on the HS waveform. Each candidate feature $X_i$ can be characterized by a respective feature timing indication $TX_i$ indicative of temporal location of $X_i$, and a respective feature intensity indication $\|X_i\|$ indicative of signal strength of $X_i$. In an example, the feature timing indication $TX_i$ can be measured as a latency from a fiducial point to $X_i$. Examples of the fiducial point can include a P wave, a Q wave, or an R wave on an electrocardiograph (ECG), a sensed or paced event on an intracardiac electrogram (EGM), or other characteristic points on a physiologic signal indicative of beginning of a cardiac cycle. In an example, the fiducial point can be a characteristic point of a HS detection window for detecting a specified HS component (e.g., S1, S2, S3, or S4), such as a starting point or middle point of the HS detection window. In an example, the HS detection window can be determined based on heart rate, time of day, or other factors. Examples of the signal strength $\|X_i\|$ can include signal amplitude, signal power, or other indicators of signal strength.

The second feature detector circuit 124 can be configured to detect a second set of one or more candidate features $\{Y_j\}$, different than $\{X_i\}$, where "j" denotes a feature index in the second candidate feature set. The second candidate feature set $\{Y_j\}$ can be detected within the same HS waveform used for detecting $\{X_i\}$. Similar to $\{X_i\}$ as discussed above, each candidate feature $Y_j$ can be a statistical or morphological feature, and characterized by a respective feature timing indication $TY_j$ indicative of temporal location and a respective feature intensity indication $Y_j$ indicative of signal strength, of the candidate feature $Y_j$.

In an example, $\{X_i\}$ or $\{Y_j\}$ can be detected within a time window associated with one of S1, S2, S3, or S4 heart sound component. The time window can be determined with reference to a physiologic event such as a Q wave, an R wave, or a QRS complex detected from a surface ECG, a subcutaneous ECG, or a cardiac sensing or pacing event in an intracardiac EGM. For example, an S1 window can begin at 50 milliseconds (msec) following a detected R wave and have duration of 300 msec. An S2 window can begin at specified offset following a detected R wave or S1 heart sound. An S3 window can be determined using at least one cardiac signal feature such as the R-wave timing or the timing of S2 heart sound. The S3 window can have a specified duration and can begin at a specified offset following the detected S2. In an example, the offset can be 125 msec, and the S3 window duration can be 125 msec. The offset or the S3 window duration can be a function of a physiologic variable such as a heart rate. For example, the offset can be inversely proportional to the heart rate, such that the S3 detection window can start at a smaller offset following the S2 at a higher heart rate. In various examples, the HS detection window can be determined based on heart rate, time of day, or other factors.

The first candidate feature set $\{X_i\}$ and the second candidate feature set $\{Y_j\}$ can be two different categories of features characterizing the specified HS component within the receive HS waveform. In various examples, the received HS waveform can include multiple peaks and troughs. The first candidate feature set $\{X_i\}$ can include one or more peaks within a portion of the HS waveform, such as a time window associated with one of S1, S2, S3, or S4 heart sound component. The second candidate feature set $\{Y_j\}$ can include one or more troughs within the same time window as that used for detecting $\{X_i\}$. For example, $\{X_i\}$ and $\{Y_j\}$ can respectively comprise peaks or troughs within the same S1 window as a portion of the received HS waveform. The signal peaks or the signal troughs can each be detected using zero-crossing of a first order difference of the windowed portion of the HS waveform, or any other liner or nonlinear methods. The signal peaks or the signal troughs can each be characterized by respective feature timing indication ($TX_i$ or $TY_j$) and respective feature intensity indication ($\|X_i\|$ or $\|Y_j\|$). For example, $TX_i$ or $TY_j$ can be respectively measured as latency between a reference point (such as R wave on an ECG or EGM, or a characteristic point such as starting point or middle point of a HS detection window) and $X_i$ or $Y_j$; and $\|X_i\|$ or can be respectively determined as the amplitude of the peak $X_i$ or the trough $Y_j$. The peaks in $\{X_i\}$ and the troughs in $\{Y_j\}$ are candidates to represent the S1 heart sound in the S1 window. In an example, $\{X_i\}$ can include one or more HS signal samples each characterizing a transition from a peak to a trough (e.g., a zero-crossing point) within a portion of the HS waveform; or $\{Y_j\}$ can include one or more HS signal samples each characterizing a transition from a trough to a peak (e.g., a zero-crossing point) within the same portion of the HS waveform.

The feature selection circuit 126, coupled to the first and second feature detector circuits 122 and 124, is configured to determine first and second selected features from respective candidate feature set. As illustrated in FIG. 1, the feature selection circuit 126 can include a feature category selector circuit 131 and a selected feature detector circuit 132.

The feature category selector circuit 131 can produce an inter-categorical metric $M_{XY}$ indicative of temporal relationship between $\{X_i\}$ and $\{Y_i\}$ such as respectively produced by the first and second feature detector circuits 122 and 124, and select at least one of the feature sets, $\{X_i\}$ or $\{Y_i\}$, for feature optimization at least based on the inter-categorical metric $M_{XY}$. In an example, the feature category selector circuit 131 can be configured to track changes ($\Delta M_{XY}$) of $M_{XY}$ over time such as over multiple physiological cycles, and to track changes ($\Delta X$ or $\Delta Y$, respectively) of one or both of $\{X_i\}$ and $\{Y_i\}$ over time such as over multiple physiological cycles. The feature category selector circuit 131 can then select at least one feature set between $\{X_i\}$ or $\{Y_i\}$ for optimization based on one or more of the tracked changes $\Delta M_{XY}$, $\Delta X$, or $\Delta Y$. Examples of the feature category selector circuit 131 are described below, such as with reference to FIGS. 2-4.

The selected feature detector circuit 132 can be configured to determine a selected feature from the selected candidate feature set, such as a first selected feature $X_{Opt}$ from $\{X_i\}$, or a second selected feature $Y_{Opt}$ from $\{Y_i\}$. The selected feature can be selected as a candidate feature that meets a specified criterion when compared to other candidate features of the selected feature set. In an example, the selected feature detector circuit 132 can determine, for each candidate feature of the selected feature set, a variability index of the feature timing indications. The variability index can be computed as a deviation of the feature timing indication of the candidate feature from a reference timing indication. The selected feature detector circuit 132 can then determine the selected feature to be the candidate feature with a corresponding variability index value smaller than any other candidate features in the selected feature set. For example, assume the feature category selector circuit 131 selects the first feature set $\{X_i\}$ for feature optimization, and $\{X_i\}$ includes N detected peaks within a specified S1 window of a HS waveform, i.e., $\{X_i\}$ for i=1, 2, ..., N. The selected feature detector circuit 132 can compute, for each detected peak $X_i$, a respective variability index $\Delta TX_i = TX_i - TX_{Ref}$, where $TX_{Ref}$ denotes a specified reference timing indication. The selected feature detector circuit 232 can then determine the selected feature $X_{Opt}$ that minimizes the variability index among the candidate features $\{X_i\}$, i.e., $X_{Opt}$=argmin $(TX_i - TX_{Ref})$ for i=1, 2, ..., N.

In an example, the reference timing indication $TX_{Ref}$ can be time-varying and computed using timing indications associated with one or more historical selected features such as obtained from a plurality of historical HS waveforms, hereinafter referred to as "historical timing indications". For example, let $X_{Opt}$(t) denote the optimal peak to be determined from the present HS waveform at present time t, and $X_{Opt}$(t') denote the optimal peak detected from a historical HS waveform at a historical time t' (t'<t). The reference timing indication $TX_{Ref}$(t) can then be computed using one or more historical feature timing indications $\{TX_{Opt}(t')\}$, i.e., $TX_{Ref}(t)=\varphi(\{TX_{Opt}(t')\}$, for one or more t'<t. In an example, $TX_{Ref}$(t) can be computed as a mean, a median, a mode, or other central tendency or other statistics, through the operator $\varphi$, of the historical feature timing indications $\{TX_{Opt}(t')\}$.

The heart sound recognition circuit 128, coupled to the feature selection circuit, can be configured to determine at least the HS timing parameter of the specified HS component using a comparison between the first and second selected features such as produced by the selected feature detector circuit 132. In an example, the HS recognition circuit 128 can determine the feature timing indication of the first selected feature, $TX_{Opt}$, as the HS timing parameter if the feature intensity indication of the first selected feature $X_{Opt}$ exceeds the feature intensity indication $\|Y_{Opt}\|$ of the second selected feature $Y_{Opt}$, i.e., $\|X_{Opt}\| > \|Y_{Opt}\|$. The HS recognition circuit 128 can determine the feature timing indication of the second selected feature, $TY_{Opt}$, as the HS timing parameter if $\|X_{Opt}\| \le \|Y_{Opt}\|$.

In an example, the heart sound tracking system 100 can optionally include a therapy circuit coupled to the heart sound analyzer circuit 120. The therapy circuit can be configured to automatically program one or more therapy parameters using at least the detected HS components and the HS timing parameter associated with the HS components such as produced by the feature selection circuit 126 and the HS recognition circuit 128, and deliver the therapy to a target tissue site. Examples of the therapy can include electric pacing therapy, cardioversion therapy, defibrillation therapy, neurostimulation therapy, or any other stimulation therapy using a specified energy source. Examples of the therapy parameters can include pulse amplitude, pulse waveform, pulse frequency, pulse width, duty cycle, duration, or any other parameters associated with the electrostimulation.

The controller circuit 130 can receive external programming input from the instruction receiver circuit 140 to control the operations of the heart sound receiver circuit 110, the heart sound analyzer circuit 120, and the data flow and instructions between these components. Examples of the instructions received by instruction receiver 140 can include parameters used in sensing a HS signal from a HS sensor, processing received HS information, detecting the first and second one or more candidate features from the HS information, selecting a feature set between the first and second feature sets, selecting an selected feature from the selected candidate feature set, and determining the HS timing parameter. The instruction receiver circuit 140 can include a user interface configured to present programming options to the user and receive system user's programming input.

Figure 2:
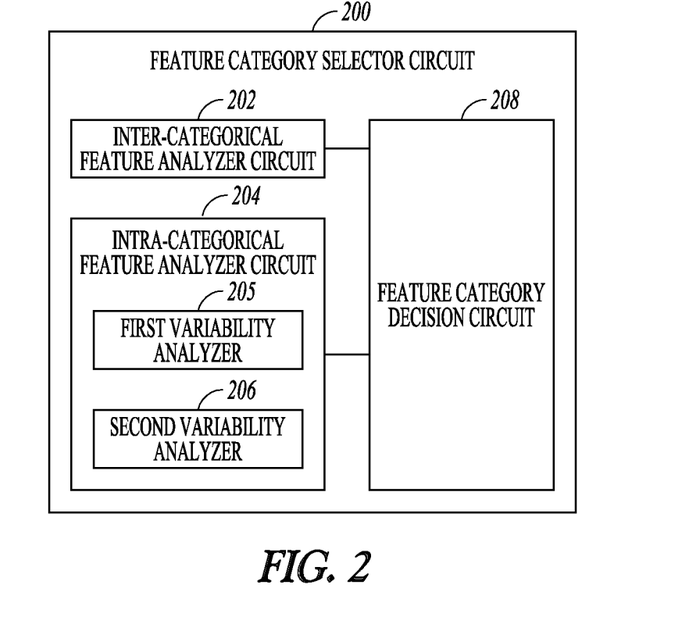
FIG. 2 illustrates an example of a feature category selector circuit used in a heart sound tracking system.

FIG. 2 illustrates an example of a feature category selector circuit 200, which can be an embodiment of the feature category selector circuit 131. The feature category selector circuit 200 can include an inter-categorical feature analyzer circuit 202, an intra-categorical feature analyzer circuit 204, and a feature category decision circuit 208.

The inter-categorical feature analyzer circuit 202 can be configured to compute an inter-categorical metric $M_{XY}$ using the first and second sets of candidate features $\{X_i\}$ and $\{Y_j\}$, such as provided respectively by the first and second feature detector circuits 122 and 124. In an example, the inter-categorical metric $M_{XY}$ can include a temporal offset $D_{XY}$ indicative of temporal relationship between $\{X_i\}$ and $\{Y_j\}$. The feature category decision circuit 208 can determine first or second features, $X_{Opt}$ or $Y_{Opt}$ respectively, at least in response to $D_{XY}$ meeting a specified criterion.

The temporal offset $D_{XY}$ can be computed as timing difference between a first feature timing indication ($TX_p$) of a first candidate feature $X_p$ and a second timing indication ($TY_q$) of a second candidate feature $Y_q$, i.e., $D_{XY}=|TX_p - TY_q|$. In an example, the first candidate feature $X_p$ can be selected from $\{X_i\}$ such that $TX_p$ is closest to a central tendency of the feature timing indications $\{TX_i\}$. The second candidate feature $Y_q$ can be similarly selected from $\{Y_j\}$ such that $TY_q$ is closest to a central tendency of the feature timing indications $\{TY_j\}$. In an example, $X_p$ and $Y_q$ can be determined using a heart sound template, such as system and methods for tracking heart sounds as described in Patangay et al., U.S. Pat. No. 7,853,327 entitled "HEART SOUND TRACKING SYSTEM AND METHOD," which is hereby incorporated by reference in its entirety.

In an example, the temporal offset $D_{XY}$ can be computed as difference between a first central tendency of $\{TX_i\}$ and a second central tendency of $\{TY_j\}$, i.e., $D_{XY}=|\varphi(\{TX_i\})-\varphi(\{TY_j\})|$, where $\varphi$ is a central tendency function. In yet another example, $D_{XY}$ can be computed as a central tendency of pair-wise temporal offsets between $\{X_i\}$ and $\{Y_j\}$, i.e., $D_{XY}=\varphi(\{|TX_i-TY_j|\})$ for i=1, 2, ..., N and j=1, 2, ..., M, where N denotes the number of first candidate features and M the number of second candidate features. Examples of the central tendency can include mean, median, mode, or other measures of centrality. Other statistics, such as quartiles, deciles, or percentiles can also be used to calculate $D_{XY}$.

The intra-categorical feature analyzer circuit 204 can include a first variability analyzer circuit 205 and a second variability analyzer circuit 206. The first variability analyzer circuit 205 can be configured to determine a first variability index $\Delta TX$ indicative of temporal variation of the feature timing indications of the first candidate features. Similarly, the second variability analyzer circuit 206 can be configured to determine a second variability index $\Delta TY$ indicative of temporal variation of the feature timing indications of the second candidate features. In various examples, the temporal variation can include a timing difference between the feature timing indications measured at different time such as during different physiological cycles. For example, $\Delta TX$ can be computed as a timing difference between a central tendency of $\{TX_i\}$ at time t (such as corresponding to the HS waveform at present physiological cycle) and the feature timing indication of the first selected feature $TX_{Opt}$ at an earlier time t' (such as corresponding to the HS waveform at a previous physiological cycle), i.e., $\Delta TX=\varphi(\{TX_i\}(t))-TX_{Opt}(t')$. Similarly, $\Delta TY$ can be computed as a timing difference between a central tendency of $\{TY_j\}$ at time t (such as corresponding to the HS waveform at present physiological cycle) and the feature timing indication of the second selected feature $TY_{Opt}$ at an earlier time t' (such as corresponding to the HS waveform at a previous physiological cycle), i.e., $\Delta TY=\varphi(\{TY_j\}(t))-TY_{Opt}(t')$.

The feature category decision circuit 208, coupled to both the inter-categorical feature analyzer circuit 202 and the intra-categorical feature analyzer circuit 204, can choose sets a feature set between the first and second candidate feature sets for optimization in response to one or more of the inter-categorical metric $M_{XY}$, the first variability index $\Delta TX$, and the second variability index $\Delta TY$ meeting respective criteria. In an example, the feature category decision circuit 208 can optimize the first or second selected feature only if the inter-categorical metric $M_{XY}$ falling within a specified range. If $M_{XY}$ falls within the specified range, no feature optimization is performed, and a representative first feature $X_{Rep}$ and a representative second feature $Y_{Rep}$ can be respectively determined using a heuristic method, such as the candidate feature having the timing indication closest to the median or mean of the $\{TX_i\}$ or $\{TY_j\}$. Alternatively, $X_{Rep}$ and $Y_{Rep}$ can be respectively determined as the first and second candidate features $X_p$ and $Y_q$ based on a heart sound template, such as system and methods for tracking heart sounds as described in Patangay et al., U.S. Pat. No. 7,853,327 entitled "HEART SOUND TRACKING SYSTEM AND METHOD," which is hereby incorporated by reference in its entirety.

If $M_{XY}$ falls outside the specified range, the feature category decision circuit 208 can initiate feature optimization by selecting the first feature set $\{X_i\}$ for optimization in response to the first variation index $\Delta TX$ exceeds a specified threshold; or selecting the second feature set $\{Y_j\}$ for optimization in response to the second variation index $\Delta TY$ exceeds a specified threshold. The selected feature set, $\{X_i\}$ or $\{Y_j\}$, can then be used by the selected feature detector circuit 132 to determine selected first feature $X_{Opt}$ from $\{X_i\}$ or the selected second feature $Y_{Opt}$ from $\{Y_j\}$.

Figure 3:
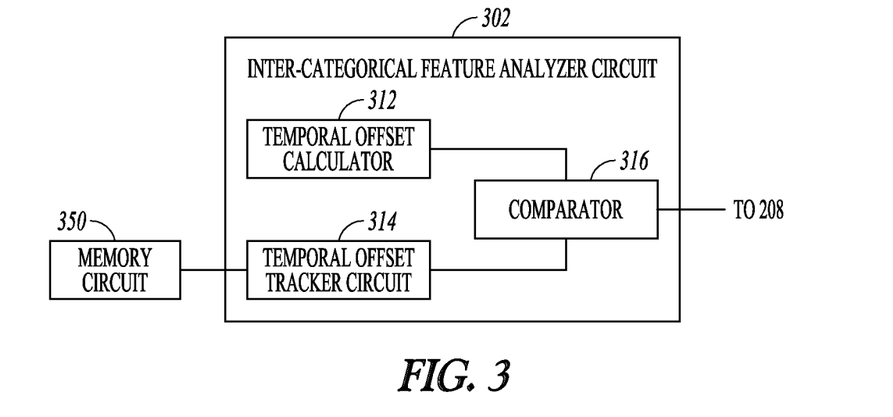
FIG. 3 illustrates an example of an inter-categorical feature analyzer circuit used in a heart sound tracking system.

FIG. 3 illustrates an example of the inter-categorical feature analyzer circuit 302, which can be an embodiment of the inter-categorical feature analyzer circuit 202. The inter-categorical feature analyzer circuit 302 can include a temporal offset calculator 312, a temporal offset tracker circuit 314, and a comparator 316.

The temporal offset calculator 312 can be configured to compute a present temporal offset $D_{XY}(t)$ at time t between the first and second sets of candidate feature $\{X_i\}$ and $\{Y_j\}$. As discussed above with respect to the inter-categorical feature analyzer circuit 202, the temporal offset $D_{XY}$ can be computed as a timing difference between a first feature timing indication ($TX_p$) of the first candidate feature $X_p$ and the second timing indication ($TY_q$) of the second candidate feature $Y_q$ at time t, such as corresponding to a present HS waveform. The temporal offset tracker circuit 314 can be coupled to a memory circuit 350 that can operatively store multiple historical temporal offsets $D_{XY}(t')$ at historical time t' prior to the present time t (t'<t), such as corresponding to a plurality of historical HS waveforms. In an example, the historical temporal offsets $D_{XY}(t')$ can be computed as a difference between the timing indication of the selected first feature, $TX_{Opt}(t')$, and the timing indication of the selected second feature, $TY_{Opt}(t')$, i.e., $D_{XY}(t')=|TX_{Opt}(t')-TY_{Opt}(t')|$. Both $TX_{Opt}(t')$ and $TY_{Opt}(t')$ can be obtained respectively from the selected first feature and the selected second feature from a historical HS waveform obtained at time t'.

The temporal offset tracker circuit 314 can receive from the memory circuit 350 one or more of the historical temporal offsets $D_{XY}(t')$, and track temporal variation of the historical temporal offsets. In an example, the temporal offset tracker circuit 314 can compute a reference temporal offset $D_{Ref}$ using the one or more historical temporal offsets. In an example, the reference temporal offset $D_{Ref}$ can be computed as a median, a mean, a mode, a weighted average, or other central tendency or statistics of the one or more historical temporal offsets.

The comparator 316, coupled to the temporal offset calculator 312 and the temporal offset tracker circuit 314, can be configured to compare the present temporal offset $D_{XY}$ with the reference temporal offset $D_{Ref}$, and to produce an indication of whether $D_{XY}$ falls within a specified margin of $D_{Ref}$.

Figure 4:
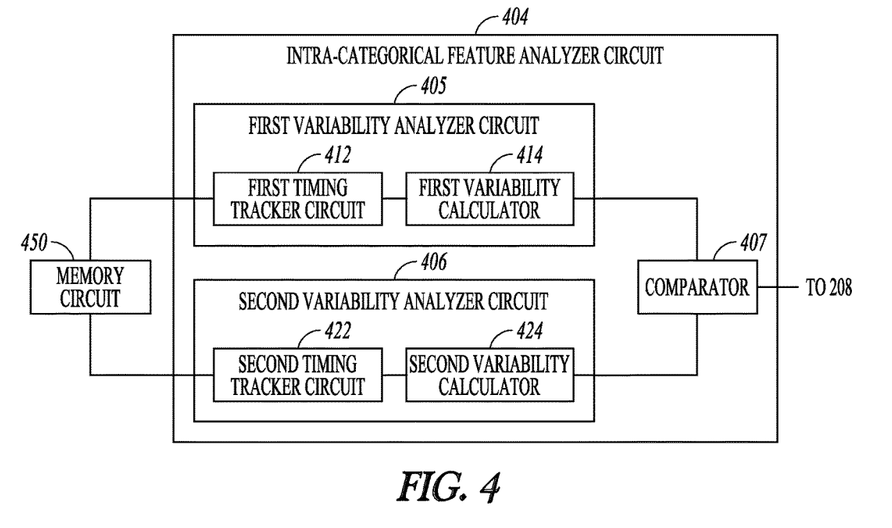
FIG. 4 illustrates an example of an intra-categorical feature analyzer circuit used in a heart sound tracking system.

FIG. 4 illustrates an example of an intra-categorical feature analyzer circuit 404, which can be an embodiment of the intra-categorical feature analyzer circuit 204. The intra-categorical feature analyzer circuit 404 can include a first variability analyzer circuit 405 and a second variability analyzer circuit 406. At least one of the first or second variability analyzer circuits can be coupled to a memory circuit 450. The memory circuit 450 can operatively store timing indications of historical selected first features, $TX_{Opt}(t')$, and timing indications of historical selected second features, $TY_{Opt}(t')$, for some historical time t', such as associated with a plurality of historical HS waveforms.

The first variability analyzer circuit 405 can include a first timing tracker circuit 412 and a first variability calculator 414. The first timing tracker circuit 412 can receive from the memory circuit 450 one or more historical first timing indications $TX_{Opt}(t')$, and track temporal variation of $TX_{Opt}(t')$. The first timing tracker circuit 412 can compute a first reference timing indication $TX_{Ref}$ using the one or more of $TX_{Opt}(t')$. In an example, $TX_{Ref}$ can be the timing indication of the optimal peak determined from a HS waveform immediately preceding the present HS waveform. In another example, $TX_{Ref}$ can be computed as a median, a mean, a mode, a weighted average, or other central tendency or statistics of $TX_{Opt}(t')$. The first variability calculator 414 can be configured to compare the timing indication of the first feature, such as the first feature timing indication ($TX_p$) of the first candidate feature $X_p$, with the first reference timing indication $TX_{Ref}$, and to produce a first variability index $\Delta TX$ indicative of a deviation of $TX_p$ from the first reference timing indication $TX_{Ref}$, e.g., $\Delta TX = TX_p - TX_{Ref}$.

Similarly, the second variability analyzer circuit 406 can include a second timing tracker circuit 422 and a second variability calculator 424. The second timing tracker circuit 422 can receive from the memory circuit 450 one or more historical second timing indications $TY_{Opt}(t')$, and track temporal variation of $TY_{Opt}(t')$. The second timing tracker circuit 422 can compute a second reference timing indication $TY_{Ref}$ using the one or more of $TY_{Opt}(t')$. In an example, $TY_{Ref}$ can be the timing indication of the optimal trough determined from a HS waveform immediately preceding the present HS waveform. In another example, $TY_{Ref}$ can be computed as a median, a mean, a mode, a weighted average, or other central tendency or statistics of $TY_{Opt}(t')$. The second variability calculator 424 can be configured to compare the timing indication of the second feature, such as the second feature timing indication ($TY_q$) of the second candidate feature $Y_q$, with the second reference timing indication $TY_{Ref}$, and to produce a second variability index $\Delta TY$ indicative of a deviation of $TY_q$ from the second reference timing indication $TY_{Ref}$, e.g., $\Delta TY = TY_q - TY_{Ref}$.

The comparator 407, coupled to the first and second variability calculators 414 and 424, can be configured to compare the first ($\Delta TX$) and second variability indices ($\Delta TY$), and to produce an indication of whether a relative difference between $\Delta TX$ and $\Delta TY$ exceeds a specified margin.

As illustrated in FIGS. 3 and 4, the indication of whether the temporal offset $D_{XY}$ falls within a specified margin of $D_{Ref}$, such as produced by the comparator 316, and the indication of whether a relative difference between $\Delta TX$ and $\Delta TY$ exceeds a specified margin, such as produced by the comparator 407, can be received by the feature category decision circuit 208, which determines which feature set to undergo optimization based on $D_{XY}$ and the comparison between $\Delta TX$ and $\Delta TY$. In an example, the feature category decision circuit 208 can select the first set of candidate features $\{X_i\}$ for optimization in response to (1) the temporal offset $D_{XY}$ exceeds $D_{Ref}$ by a specified margin and (2) the first variability index $\Delta TX$ exceeds the second variability index $\Delta TY$ by a first specified threshold. The feature category decision circuit 208 can select the second set of candidate features $\{Y_i\}$ for optimization in response to (1) the temporal offset $D_{XY}$ exceeds $D_{Ref}$ by a specified margin and (2) the second variability index $\Delta TY$ exceeds the first variability index $\Delta TX$ by a second threshold.

Figure 5:
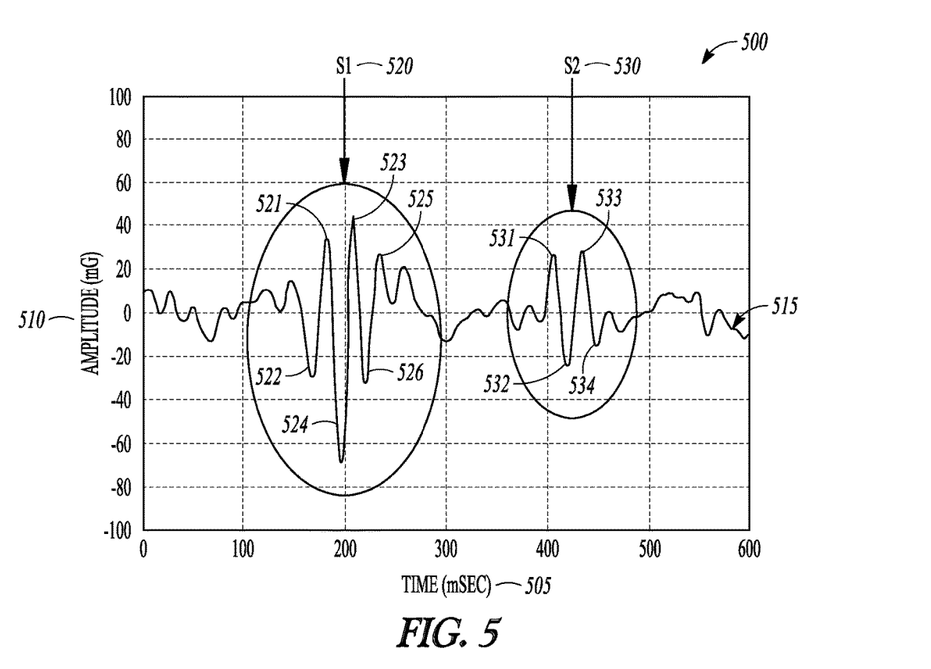
FIG. 5 illustrates an example of a portion of a heart sound signal including a HS waveform.

FIG. 5 illustrates an example of a portion of a heart sound (HS) signal 500, which includes a HS waveform 515. The HS waveform 515 can be extracted from one cardiac cycle of the HS signal a particular time, or an ensemble average of a HS signal over multiple cardiac cycles or other physiological cycles. The HS waveform 515 can include an S1 component 520 and an S2 component 530, shown with respect to Amplitude (mG) 510 and Time (msec) 505, where mG are units of acceleration that are produced when an accelerometer is used to measure the vibrations produced by the heart sounds.

The HS waveform 515, as well as individual HS component, can include multiple peaks and multiple troughs. As illustrated in FIG. 5, the S1 component 520 includes peaks 521, 523 and 525, and troughs 522, 524 and 526. The S2 component 530 portion of the HS waveform includes peaks 531 and 533, and troughs 532 and 534. In detecting the S1 or S2 heart sound, the heart sound tracking system 100 can be used to determine for S1 or S2 component the respective timing and intensity parameters. In an example, the timing parameter of the S1 heart sound can be determined as the timing of one of the peaks 521, 523 and 525, or one of the troughs 522, 524 and 526. Similarly, the timing parameter of the S2 heart sound can be determined as the timing of one of the peaks 531 and 533, or one of the troughs 532 and 534.

The HS waveform can be received by the heart sound receiver circuit 110, and an S1 window can be applied to the HS waveform 515. In an example, the S1 window can begin at 50 milliseconds (msec) following a detected R wave of an ECG signal and have duration of 300 msec. The ECG signal can be synchronously acquired with the HS sound signal. The first feature detector circuit 122 can detect the first set of candidate features including the peaks 521, 523 and 525. The second feature detector circuit 124 can detect the second set of candidate features including the troughs 522, 524 and 526. The timing indications of each peak or trough can be measured as latency between the R wave and the respective peak or trough. The feature category selector circuit 131 or the feature category selector circuit 200 can produce an inter-categorical metric, such as a temporal offset $D_{XY}$. In an example, the temporal offset $D_{XY}$ can be computed as a difference between the median (or other central tendency or statistics) of the timing indications of the peaks 521, 523 and 525 and the median (or other central tendency or statistics) of the timing indications of the troughs 522, 524 and 526, such as by using the inter-categorical feature analyzer circuit 202 or the inter-categorical feature analyzer circuit 302.

The peaks 521, 523 and 525 can be processed by the first variability analyzer circuit 205 or the first variability analyzer circuit 405 to determine a first variability index $\Delta TX$, such as a difference between a first feature timing indication (e.g., the median of the timing indications of the peaks 521, 523 and 525) and a reference timing indication of the peaks, $TX_{Ref}$. Similarly, the troughs 522, 524 and 526 can be processed by the second variability analyzer circuit 206 or the second variability analyzer circuit 406 to determine a second variability index $\Delta TY$, such as a difference between a second feature timing indication (e.g., the median of the timing indications of the troughs 522, 524 and 526) and a reference timing indication of the troughs, $TY_{Ref}$. Both $TX_{Ref}$ and $TY_{Ref}$ can be respectively computed as a median, a mean, a mode, a weighted average, or other central tendency or statistics of historical timing indications of the optimal peaks or troughs.

The inter-categorical temporal offset $D_{XY}$, the first variability index $\Delta TX$, and the second variability index $\Delta TY$ can be used, such as by the feature category decision circuit 208, to determine if a feature optimization process is warranted. If $D_{XY}$ exceeds a specified threshold value, or exceeds a reference temporal offset $D_{Ref}$ (such as determined by the temporal offset tracker circuit 314 using one or more historical temporal offsets) by a specified margin, then it indicates either the first feature timing indication or the second feature timing indication substantially deviates from their respective historical reference timing indications. Therefore, an optimization process is deemed necessary. To determine which feature set needs to be optimized, the first variability index $\Delta TX$ can be compared to the second variability index $\Delta TY$, such as operated by the intra-categorical feature analyzer circuit 404. The feature set of the peaks 521, 523 and 525 can be selected for optimization if $\Delta TX$ exceeds $\Delta TY$ by a first specified threshold; and the feature set of troughs 522, 524 and 526 can be selected for optimization if $\Delta TY$ exceeds $\Delta TX$ by a second threshold.

However, if $D_{XY}$ does not exceed the specified threshold value or falls within a specified range of the reference temporal offset Dm, neither the first feature timing indication nor the second feature timing indication is deemed to substantially deviate from their respective historical reference timing indications. Therefore, instead of the optimization process, a representative first feature $X_{Rep}$ and a representative second feature $Y_{Rep}$ can be respectively determined using a heuristic method, such as the candidate feature having the timing indication closest to the median or mean of the $\{TX_i\}$ or $\{TY_j\}$, or the candidate features based on a heart sound template, such as system and methods described in Patangay et al., U.S. Pat. No. 7,853,327 entitled "HEART SOUND TRACKING SYSTEM AND METHOD," which is hereby incorporated by reference in its entirety.

If the feature set of the peaks 521, 523 and 525 are selected for optimization, the selected feature detector circuit 132 can choose from the peaks 521, 523 and 525 an optimal peak $X_{Opt}$, such that it minimizes a difference between the timing indication of a peak and a historically tracked reference timing indication of the peaks. The optimal peak $X_{Opt}$ determined as such has a timing indication closest to the historically tracked reference timing indication of the peak. Likewise, if the feature set of the troughs 522, 524 and 526 are selected for optimization, the selected feature detector circuit 132 can choose from the troughs 522, 524 and 526 an optimal trough $Y_{Opt}$ that minimizes a difference between the timing indication of a trough and a historically tracked reference timing indication of the troughs.

The heart sound recognition circuit 128 can then determine the temporal location of S1 component within the HS component 515 by comparing the intensity indications of the optimal peak and the optimal trough. For example, if the optimal peak is peak 523 and the optimal trough is 524, and the amplitude of the trough 524 exceeds the amplitude of the peak 523 by a specified threshold, the heart sound recognition circuit 128 can choose the trough 524 and determines the timing indication of the trough 524 as the S1 timing parameter.

Figure 6:
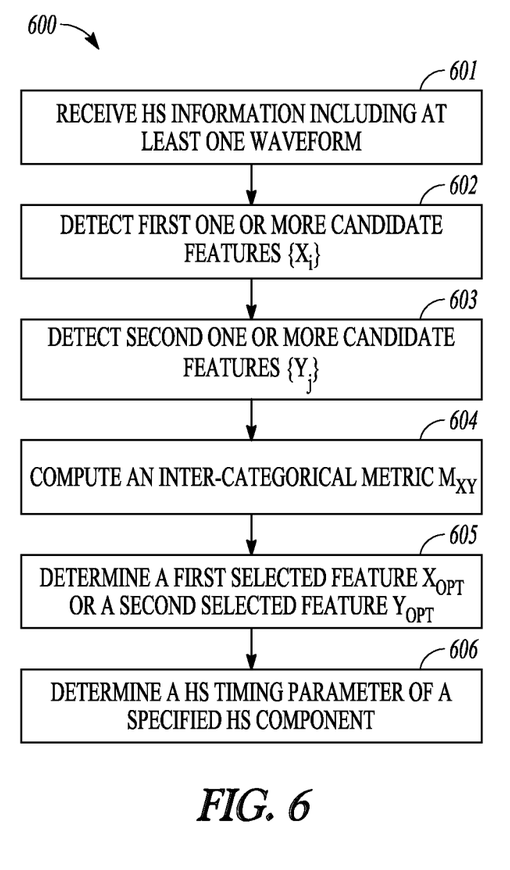
FIG. 6 illustrates an example of a method for tracking heart sounds and detecting a HS component from the HS signal.

FIG. 6 illustrates an example of a method 600 for tracking heart sounds (HS) and detecting a HS component from the HS signal. The method 600 can be implemented and operate in an implantable, wearable, or other ambulatory medical device, or in a remote patient management system. In an example, the method 600 can be performed by the heart sound tracking system 100, or any modification thereof.

The method 600 begins at step 601, where HS information can be received, such as by via a system comprising the HS receiver circuit 110 the HS information can include a HS waveform, such as a portion or entirety of a HS signal. The HS information can include information of at least one HS component, such as S1, S2, S3, or S4 heart sound. In an example, the HS waveform can include at least one ensemble average of a HS signal over multiple physiological cycles such as multiple cardiac cycles, or over a specified time period such as one minute, ten minutes, one hour, one day, etc. The HS information can be obtained by using a physiologic sensor configured to sense an electrical or optical HS signal that includes information indicative of acoustic or mechanical vibration of a heart.

At 602, a first set of candidate features, denoted by $\{X_i\}$ (where "i" denotes a feature index), can be detected from a portion of the received HS information, such as a portion of HS within a time window associated with one of S1, S2, S3, or S4 heart sound component. The candidate features $\{X_i\}$ can include statistical or morphological features, such as characteristic points on the HS waveform. In an example, the received HS waveform can include multiple peaks and troughs, and the candidate features $\{X_i\}$ can include signal peaks within a portion of the HS waveform. In an example, $\{X_i\}$ can include one or more HS signal samples each characterizing a transition from a peak to a trough (e.g., a zero-crossing point) within a portion of the HS waveform. Each candidate feature $X_i$ can include a feature timing indication $TX_i$ indicative of temporal location of $X_i$, and a respective feature intensity indication $\|X_i\|$ indicative of signal strength of $X_i$. The signal peaks can each be characterized by respective feature timing indication $TX_i$ (e.g., peak location with respect to a reference point such as R wave on an ECG or EGM) and feature intensity indication $\|X_i\|$ (e.g., peak amplitude).

At 603, a second set of candidate features, denoted by $\{Y_j\}$ (where "j" denotes a feature index) can be detected from a portion of the received HS information. The candidate features $\{Y_j\}$ can be detected within the same HS waveform used for detecting $\{X_i\}$. In an example, the candidate features $\{Y_j\}$ can include signal troughs within the same portion of the HS waveform for detecting the candidate features $\{X_i\}$. In an example, $\{Y_j\}$ can include one or more HS signal samples each characterizing a transition from a trough to a peak (e.g., a zero-crossing point) within the same portion of the HS waveform used for detecting $\{X_i\}$. Similar to $\{X_i\}$ as discussed above, each candidate feature $Y_j$ can include a feature timing indication $TY_j$ indicative of temporal location, and a respective feature intensity indication $\|Y_j\|$ indicative of signal strength, of the candidate feature $Y_j$. In an example, $\{X_i\}$ or $\{Y_j\}$ can be detected within a time window associated with one of S1, S2, S3, or S4 heart sound component. The time window can be determined with reference to a physiologic event such as a Q wave, an R wave, or a QRS complex detected from a surface ECG, a subcutaneous ECG, or a cardiac sensing or pacing event in an intracardiac EGM.

At 604, an inter-categorical metric, denoted by $M_{XY}$, can be computed using $\{X_i\}$ and $\{Y_j\}$. In an example, $M_{XY}$ can be computed as timing difference between a first feature timing indication ($TX_p$) of a first candidate feature $X_p$ and a second timing indication ($TY_q$) of a second candidate feature $Y_q$, i.e., $D_{XY} = |TX_p - TY_q|$. In an example, the first candidate feature $X_p$ can be selected from $\{X_i\}$ such that $TX_p$ is closest to a central tendency of the feature timing indications {TX$_i$}. The second candidate feature Y$_q$ can be similarly selected from {Y$_j$} such that TY$_q$ is closest to a central tendency of the feature timing indications {TY$_j$}. In an example, X$_p$ and Y$_q$ can be determined using a heart sound template, such as system and methods described in Patangay et al., U.S. Pat. No. 7,853,327 entitled "HEART SOUND TRACKING SYSTEM AND METHOD," which is hereby incorporated by reference in its entirety. In another example, M$_{XY}$ can indicate temporal relationship between {X$_i$} and {Y$_i$}, such as a temporal offset D$_{XY}$ measured as a difference between a central tendency of timing indications of the first set of candidate features {X$_i$} and a central tendency of timing indication of the second set of candidate features {Y$_j$} within the same time window of the HS waveform, i.e., D$_{XY}$=|φ({TX$_i$})−φ({TY$_j$})|, where {TX$_i$} and {TY$_j$} respectively denote timing indications of the candidate features {X$_i$} and {Y$_i$}, and φ is a central tendency operator, such as a mean, median, mode or other statistics of centrality.

At 605, one or both of a first selected feature X$_{Opt}$ and a second selected feature Y$_{Opt}$ can be selected from the respective candidate features set {X$_i$} and {Y$_i$}. In an example, the inter-categorical metric M$_{XY}$ can be tracked over time such as over multiple physiological cycles to compute a reference inter-categorical metric M$_{Ref}$. Additionally, one or both of the first and second candidate features {X$_i$} and {Y$_i$} can be tracked over time such as over multiple physiological cycles, and respective reference timing indications can be computed. A deviation of M$_{XY}$ (or the temporal offset D$_{XY}$) from the reference inter-categorical metric M$_{Ref}$ (or the reference temporal offset D$_{Ref}$), and a deviation of timing indications of {X$_i$} or {Y$_i$} from the respective reference timing indications, can be computed. A decision of selecting at least one feature set between {X$_i$} or {Y$_i$} can be made in response to ΔM$_{XY}$, ΔTX, or ΔTY meeting their respectively specified criterion. Among the candidate feature in the selected feature set, a selected feature, such as a first selected feature X$_{opt}$ from {X$_i$}, or a second selected feature Y$_{opt}$ from {Y$_i$}, can be selected using at least a comparison among the candidate features of the selected feature set. Examples of choosing between the first and second feature set to optimize is discussed below, such as with reference to FIG. 7.

At 606, a HS timing parameter of a specified HS component, such as timing parameter of S1 heart sound within the HS waveform, can be determined using a comparison between the first and second selected features. In an example, the HS timing parameter can be chosen as the timing indication of the first selected feature if the first selected feature has a higher intensity (e.g., amplitude of the optimal peak) than the second selected feature (e.g., amplitude of the optimal trough), and vice versa.

Figure 7:
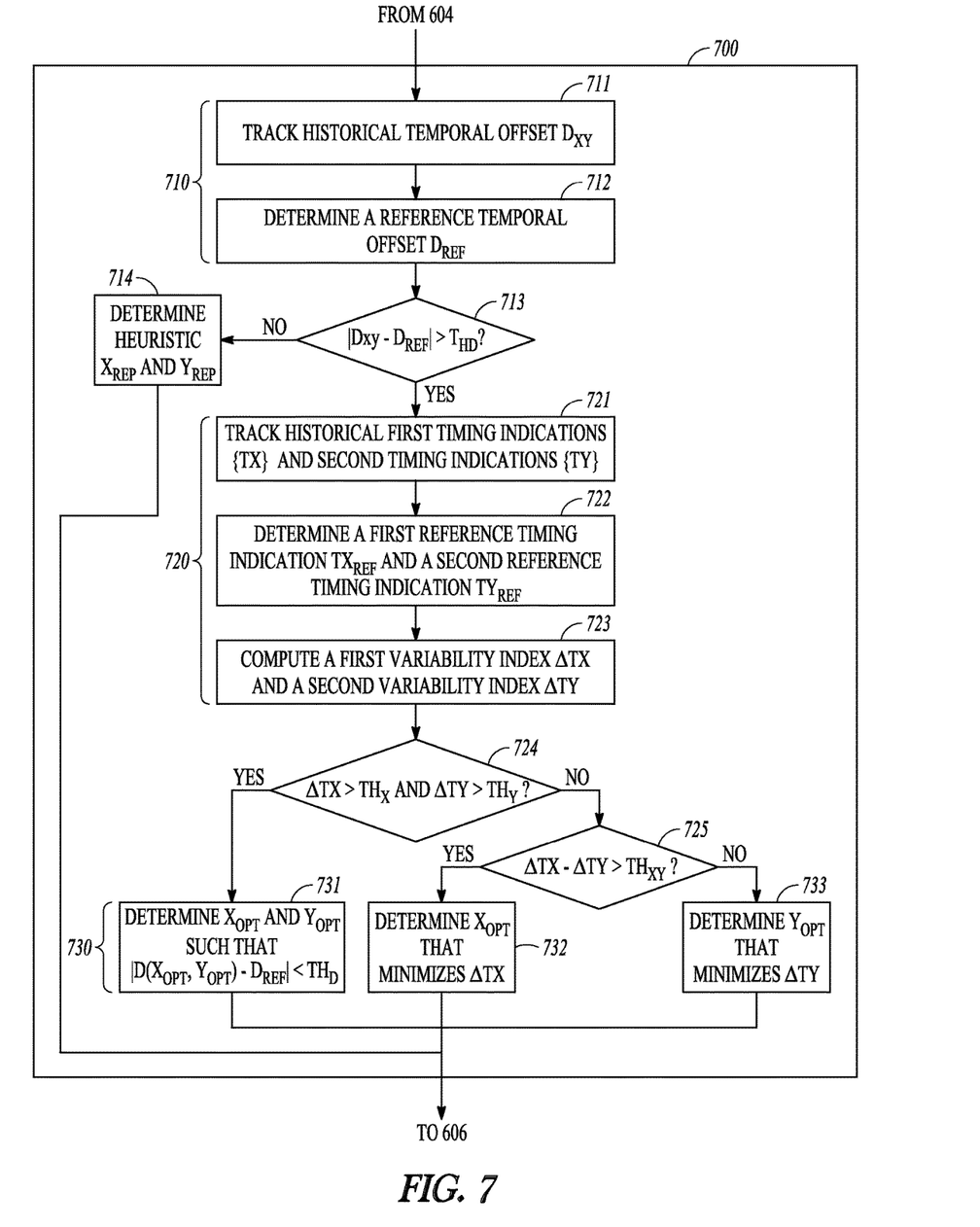
FIG. 7 illustrates an example of a method 700 for choosing an selected feature from a candidate feature set.

FIG. 7 illustrates an example of a method 700 for choosing a selected feature from a candidate feature set. The method 700 can be an embodiment of step 605 in FIG. 6, which provides a method of determining a first selected feature X$_{Opt}$ or a second selected feature Y$_{Opt}$. As illustrated in FIG. 7, the method 700 can comprise three processes: (1) process 710, including steps 711 through 713, which determines the necessity of feature optimization on either the first feature set or the second feature set based on at least an inter-categorical metric M$_{XY}$, such as an inter-categorical temporal offset D$_{XY}$; (2) process 720, including steps 721 through 725, which chooses between the first and second feature set for optimization based on at least variability indices of the first and second candidate features; and (3) process 730, including steps 731 through 733, which determines an selected feature among the candidate features of the selected feature set.

At 711, the inter-categorical metric M$_{XY}$, such as temporal offset D$_{XY}$, can be tracked. In an example, multiple historical temporal offsets D$_{XY}$(t') at historical time t' prior to the present time t (i.e., t'<t), such as associated with a plurality of historical HS waveforms, can be computed and stored in a memory. The temporal offsets D$_{XY}$(t') can be computed as a difference between the timing indication of the selected first feature (TX$_{Opt}$ (t')) and the timing indication of the selected second feature (TY$_{Opt}$ (t') at historical time t', i.e., D$_{XY}$(t')=|TX$_{Opt}$ (t)−TY$_{Opt}$(t')|, where TX$_{Opt}$ (t') and TY$_{Opt}$(t') can be obtained respectively from the selected first feature and the selected second feature from HS waveform obtained at historical time t'.

At 712, a reference temporal offset D$_{Ref}$ can be computed using one or more of the multiple historical temporal offsets D$_{XY}$(t'). In an example, D$_{Ref}$ can be computed as a median, a mean, a mode, a weighted average, or other central tendency or statistics of the one or more historical temporal offsets.

At 713, the inter-categorical metric M$_{XY}$ computed at 604, such as the temporal offset D$_{XY}$ at time t corresponding to a present HS waveform, is compared to the reference temporal offset D$_{Ref}$. If the difference between D$_{XY}$ and D$_{Ref}$ is less than or equal to a specified threshold TH$_D$, neither the first nor the second candidate features are deemed to substantially deviate from their respective reference timing indications. Therefore, no subsequent optimization process 720 is deemed necessary; and a representative first feature X$_{Rep}$ and a representative second feature Y$_{Rep}$ can be respectively determined at 714 using a heuristic method, such as the candidate feature having the timing indication closest to the median or mean of the {TX$_i$} or {TY$_j$}.

If at 713 the difference between D$_{XY}$ and D$_{Ref}$ exceeds the specified threshold TH$_D$, then it indicates either the first or the second candidate feature set substantially deviates from respective historical reference timing indications. Therefore, optimization process 720 is deemed necessary to choose between the first and second feature sets for optimization.

At 721, first timing indications {TX} of the first feature set and second timing indications {TY} of the second feature set can be tracked. In an example, multiple timing indications (TX$_{Opt}$(t')) of historical selected first features at historical time t' prior to the present time t (i.e., t'<t), such as associated with a plurality of historical HS waveforms, can be retrievably stored in a memory. Likewise, multiple timing indications (TY$_{Opt}$(t')) of historical selected second features at historical time t' can also be stored in the memory.

At 722, one or more historical first timing indications TX$_{Opt}$(t') can be retrieved from the memory, and a first reference timing indication TX$_{Ref}$ can be computed using the one or more historical first timing indications. Likewise, one or more historical second timing indications TY$_{Opt}$(t') can be retrieved from the memory, and a second reference timing indication TY$_{Ref}$ can be computed using the one or more historical second timing indications. In an example, TX$_{Ref}$ or TY$_{Ref}$ can be the timing indication of the respective selected first feature or the selected second feature determined from a HS waveform immediately preceding the present HS waveform. In another example, TX$_{Ref}$ or TY$_{Ref}$ can be computed as a median, a mean, a mode, a weighted average, or other central tendency or statistics of TX$_{Opt}$(t') and TY$_{Opt}$(t'), respectively.

At 723, a first variability index ΔTX and a second variability index ΔTY can be computed. The first variability index ΔTX can indicate a deviation of a first feature timing indication $TX_p$ from the first reference timing indication $TX_{Ref}$, and the second variability index ΔTY can indicate a deviation of a second feature timing indication $TX_q$ of the timing indications of the first set of candidate features from the second reference timing indication $TY_{Ref}$.

At 724, the first variability index ΔTX and a second variability index ΔTY can be compared to their respective threshold $TH_X$ and $TH_Y$. If both ΔTX and ΔTY exceed their respective threshold, both the first and second feature sets are deemed to substantially deviate from their respective historically determined reference timing indications. Then at 731, the selected feature of the first feature set, $X_{Opt}$, and the selected feature of the second feature set, $Y_{Opt}$, can be selected from the respective feature sets, such that the timing difference between the first and second selected features, $d(X_{Opt}, Y_{Opt})=|TX_{Opt}-TY_{Opt}|$, is within the specified margin $TH_D$ of the reference temporal offset $D_{Ref}$, i.e., $|d(X_{Opt}, Y_{Opt})-D_{Ref}|<TH_D$. In an example, $X_{Opt}$ and $Y_{Opt}$ can be determined using an exhaustive search algorithm in a search space comprising candidate feature pairs $\{(X_i, Y_j)\}$ for i=1, 2, ..., N and j=1, 2, ..., M, where N and M denote the number of features in the first and second candidate feature sets, respectively. By computing the pair-wise timing difference $d(X_i, Y_j)$, searching for $(X_{Opt}, Y_{Opt})$ can be terminated when $|d(X_i, Y_j)-D_{Ref}|<TH_D$. Other algorithms, such as greedy search algorithm, divide and conquer algorithm, binary search trees, among other search or optimization algorithms, can also be used to search for $(X_{Opt}, Y_{Opt})$ within $\{(X_i, Y_i)\}$.

If at 724 at least one of the first variability index ΔTX or the second variability index ΔTY exceeds their respective threshold $TH_X$ or $TH_Y$, then at least one of the features sets is deemed to substantially deviate from its respective reference timing indication. To determine which feature set needs to be optimized, the first variability index ΔTX can be compared to the second variability index ΔTY at 725. If ΔTX exceeds ΔTY by at least a specified threshold $TH_{XY}$, the first feature set is chosen to be optimized, and an selected first feature $X_{Opt}$ can be selected from $\{X_i\}$ at 732. However, if at 725 the difference between ΔTX and ΔTY is bounded by $TH_{XY}$ or ΔTY exceeds ΔTX, the second feature set is chosen to be optimized, and an selected second feature $Y_{Opt}$ can be selected from $\{Y_j\}$ at 733. The selected first or second feature, $X_{Opt}$ and $Y_{Opt}$, can be respectively determined as a candidate feature having a variability index smaller than any other candidate features in the respective feature set, i.e., $X_{Opt}=\text{argmin }(TX_i-TX_{Ref})$ for i=1, 2, ..., N, or $Y_{Opt}=\text{argmin }(TY_j-TX_{Ref})$ for j=1, 2, ..., M. The selected features determined at 731, 732, or 733 can then be used to determine the HS timing parameter of the specified HS component at 606.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
 a microprocessor circuit including a heart sound (HS) analyzer circuit configured to:
  receive HS information of a patient;
  detect, using the received HS information within a cardiac cycle, first one or more candidate features and different second one or more candidate features;

generate, over multiple cardiac cycles, a first track of timings of a first initial feature selected from the first one or more candidate features and a second track of timings of a second initial feature selected from the second one or more candidate features;

identify one of the first or the second track that deviates from a respective reference timing using (1) a temporal offset between the generated first and second tracks; and (2) a first variability index of the first track and a second variability index of the second track; and determine a HS timing parameter of one of an S1 S2, S3, or S4 heart sound within a cardiac cycle using the identified track, or the track that is not identified.

2. The system of claim 1, wherein:
the first one or more candidate features include one or more peaks within a specified portion of the received HS information within a cardiac cycle; and
the second one or more candidate features include one or more troughs within a specified portion of the received HS information within the cardiac cycle.

3. The system of claim 1, wherein the HS analyzer circuit is configured to:
select, for the identified track, an alternative feature from the respective one or more candidate features, the alternative feature different than the initial feature of the identified track; and
determine the HS timing parameter of one of the S1 S2, S3, or S4 heart sound within a cardiac cycle using (1) the alternative feature of the identified track and (2) the initial feature of the track that is not identified.

4. The system of claim 3, wherein:
the timing of the first initial feature includes a central tendency of timings of the first one or more candidate features, and the timing of the second initial feature includes a central tendency of timings of the second one or more candidate features.

5. The system of claim 4, further comprising a temporal offset tracker circuit configured to compute a reference temporal offset using one or more historical temporal offsets associated with a plurality of historical HS waveforms;
wherein the HS analyzer circuit is configured to identify the one of the first or the second track in response to the temporal offset falling within a specified margin of the reference temporal offset.

6. The system of claim 5, wherein the temporal offset tracker circuit is configured to compute the reference temporal offset as a central tendency of the one or more of the historical temporal offsets.

7. The system of claim 4, wherein the HS analyzer circuit is configured to:
generate the first variability index using a deviation of the timing of the first initial feature from a first reference timing indication; and
generate the second variability index using a deviation of the timing of the second initial feature from a second reference timing indication.

8. The system of claim 7, wherein at least one of the first or second reference timing indication includes a central tendency of one or more historical timing indications associated with a plurality of historical HS waveforms.

9. The system of claim 7, wherein the HS analyzer circuit is configured to:
determine from the first one or more candidate features a first selected feature that minimizes the first variability index;

determine from the second one or more candidate features a second selected feature that minimizes the second variability index; and
determine the HS timing parameter using a comparison between the first and second selected features.

10. The system of claim 9, wherein the HS analyzer circuit is configured to determine the HS timing parameter as feature timing indication of the first selected feature if a feature intensity indication of the first selected feature exceeds a feature intensity indication of the second selected feature.

11. The system of claim 1, wherein the received HS information includes at least one ensemble average of a heart sound signal over multiple physiological cycles.

12. The system of claim 11, wherein the multiple physiological cycles include multiple cardiac cycles.

13. A method of operating a medical system to detect a heart sound (HS) component, the method comprising, using a heart sound analyzer circuit:
receiving HS information
detecting, using the received HS information within a cardiac cycle, first one or more candidate features and different second one or more candidate features;
generating, over multiple cardiac cycles, a first track of timings of a first initial feature selected from the first one or more candidate features and a second track of timings of a second initial feature selected from the second one or more candidate features;
identifying one of the first or the second track that deviates from a respective reference timing using (1) a temporal offset between the generated first and second tracks; and (2) a first variability index of the first track and a second variability index of the second track; and
determining a HS timing parameter of one of an S1 S2, S3, or S4 heart sound within a cardiac cycle using the identified track, or the track that is not identified.

14. The method of claim 13, wherein receiving HS information includes receiving at least one ensemble average of a heart sound signal over multiple physiological cycles.

15. The method of claim 13, wherein detecting the first one or more candidate features includes detecting one or more peaks within a specified portion of the received HS information within a cardiac cycle, and detecting the second one or more candidate features includes detecting one or more troughs within a specified portion of the received HS information within the cardiac cycle.

16. The method of claim 13, wherein:
the timing of the first initial feature includes a central tendency of timings of the first one or more candidate features, and the timing of the second initial feature includes a central tendency of timings of the second one or more candidate features.

17. The method of claim 16, further comprising computing a reference temporal offset using one or more historical temporal offsets associated with a plurality of historical HS waveforms, wherein identifying the one of the first or the second track is in response to the temporal offset falling within a specified margin of the reference temporal offset.

18. The method of claim 16, comprising:
generating the first variability index using a deviation of the timing of the first initial feature from a first reference timing indication;
generating the second variability index using a deviation of the timing of the second initial feature from a second reference timing indication.

19. The method of claim 13, comprising:

selecting, for the identified track, an alternative feature from the respective one or more candidate features, the alternative feature different than the initial feature of the identified track; and determining the HS timing parameter of one of the S1 S2, S3, or S4 heart sound within a cardiac cycle using (1) the alternative feature of the identified track and (2) the initial feature of the track that is not identified.

20. The system of claim 1, further comprising a therapy circuit configured to initiate or adjust a therapy using the determined HS timing parameter.

* * * * *